United States Patent [19]

Cotrel

[11] Patent Number: 5,067,955
[45] Date of Patent: Nov. 26, 1991

[54] VERTEBRAL IMPLANT FOR OSTEOSYNTHESIS DEVICE

[75] Inventor: Yves P. C. Cotrel, Paris, France

[73] Assignee: Societe de Fabrication de Material Orthopedique, Berck sur Mer, France

[21] Appl. No.: 508,416

[22] Filed: Apr. 13, 1990

[30] Foreign Application Priority Data

Apr. 13, 1989 [FR] France .................. 89 04926

[51] Int. Cl.⁵ .............................................. A61F 5/01
[52] U.S. Cl. ........................................ 606/61; 606/73; 128/69; 411/398
[58] Field of Search ........................ 606/60, 61, 65, 62, 606/72, 73; 128/69; 411/372, 398, 400, 401

[56] References Cited

U.S. PATENT DOCUMENTS

| 603,891 | 5/1898 | Cassil | 411/398 X |
|---|---|---|---|
| 2,414,882 | 1/1947 | Longfellow | 606/65 |
| 2,774,350 | 12/1956 | Cleveland, Jr. | |
| 2,992,669 | 7/1961 | Fesmire | |
| 3,295,873 | 1/1967 | Attwood | 411/398 X |
| 3,997,138 | 12/1976 | Crock et al. | 606/61 X |
| 4,003,376 | 1/1977 | McKay et al. | 606/61 |
| 4,012,086 | 3/1977 | Kruse | |
| 4,041,939 | 8/1977 | Hall | 606/61 X |
| 4,124,199 | 11/1978 | Jones et al. | |
| 4,160,680 | 7/1979 | Novy et al. | |
| 4,196,944 | 4/1980 | Simatovich | |
| 4,229,875 | 10/1980 | Crispell | |
| 4,289,123 | 9/1981 | Dunn | 623/17 X |
| 4,335,838 | 10/1982 | Hickman | |
| 4,369,770 | 1/1983 | Bacal et al. | |
| 4,411,259 | 10/1983 | Drummond | |
| 4,422,451 | 12/1983 | Kalamchi | 128/69 |
| 4,433,676 | 2/1984 | Bobechko | |
| 4,567,884 | 2/1986 | Edwards | 606/61 |
| 4,569,338 | 2/1986 | Edwards | 128/69 |
| 4,641,636 | 2/1987 | Cotrel | |
| 4,713,503 | 12/1987 | Kamp | |
| 4,776,808 | 10/1988 | Davidson | |
| 4,815,453 | 3/1989 | Cotrel | 128/69 |
| 4,950,269 | 8/1990 | Gaines, Jr. | 606/61 |

FOREIGN PATENT DOCUMENTS

| 28985 | 5/1981 | European Pat. Off. |
|---|---|---|
| 128058 | 12/1984 | European Pat. Off. |
| 227594 | 7/1987 | European Pat. Off. |
| 240376 | 10/1987 | European Pat. Off. |
| 283373 | 9/1988 | European Pat. Off. |
| 1017195 | 10/1957 | Fed. Rep. of Germany . |
| 2348275 | 11/1977 | France . |
| 2369825 | 6/1978 | France . |
| 2506605 | 12/1982 | France . |
| 2545350 | 11/1984 | France . |
| 812248 | 4/1959 | United Kingdom . |
| 87/01026 | 2/1987 | World Int. Prop. O. |

OTHER PUBLICATIONS

Metal & Ceramic Biomaterials, vol. I, pp. 96–96, Copyright 1984.
Mecanique, No. 289, Jan. 1974, pp. 35–39; P. Rousseau: "Aciers Inoxydables a Hautes Caracteristiques".

Primary Examiner—Richard J. Apley
Assistant Examiner—Linda C. M. Dvorak
Attorney, Agent, or Firm—Wenderoth, Lind & Ponack

[57] ABSTRACT

This vertebral implant (1) comprises an osseous anchoring element (2), a body (3) having a channel (4) designed to be passed through by a rod (5), and a first screw (9) for securing with the rod, screwed through a clamp (20) able to slide on the rod and to take up a position in the body; this implant comprises at least one second screw (12, 13) for blocking the rod (5), passing through the body (3) laterally to the first screw (9) and engaged in a tapped hole (12a, 13a) inclined relative to the axis (XX) of the said first screw, these two screws (9, 12 or 13) being situated essentially in a phane perpendicular to the axis (YY) of the channel (4) and of the rod (5). The size of this implant is smaller than that of the known clamp and lock implants, and it can be put into position more easily and more quickly by the surgeon.

15 Claims, 4 Drawing Sheets

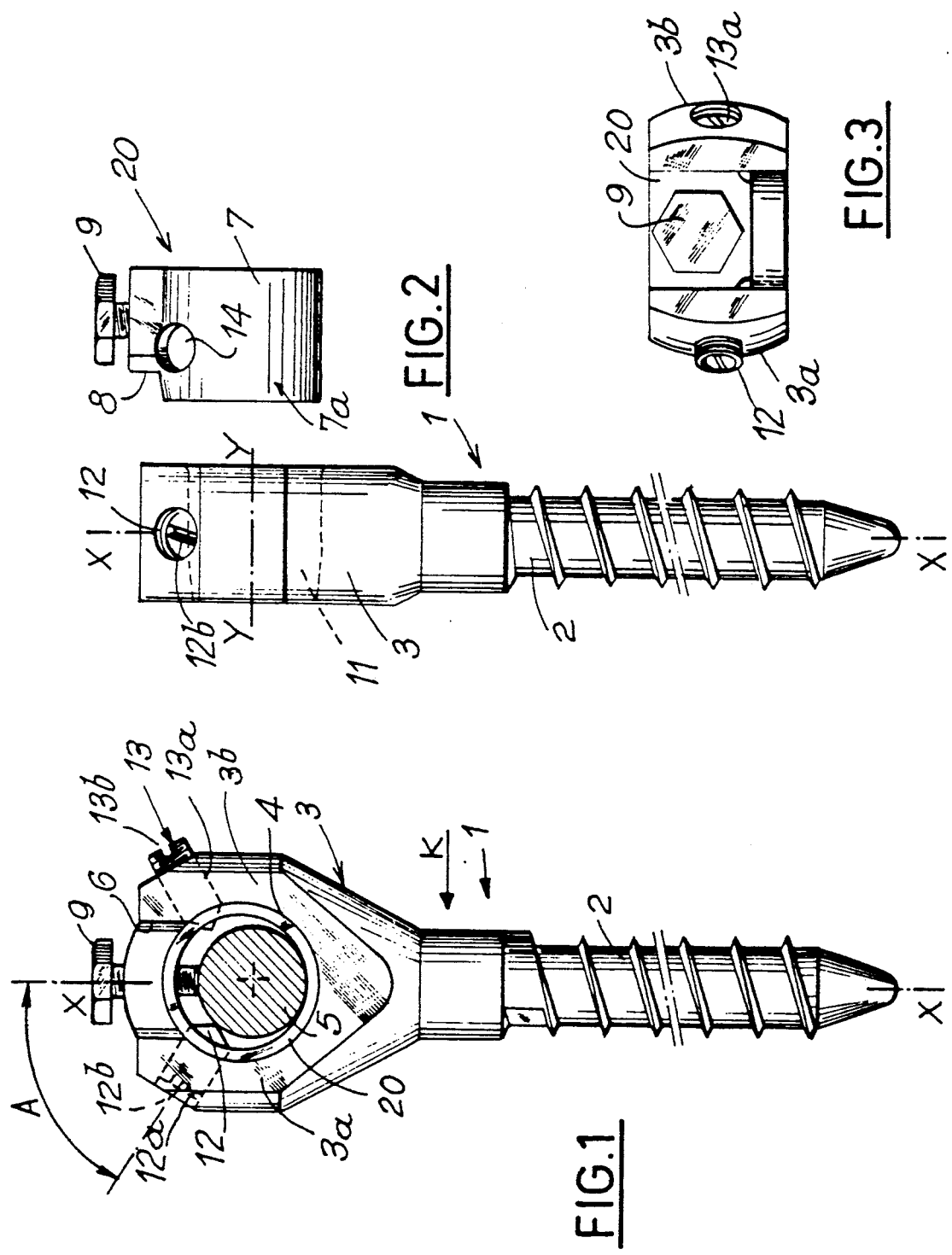

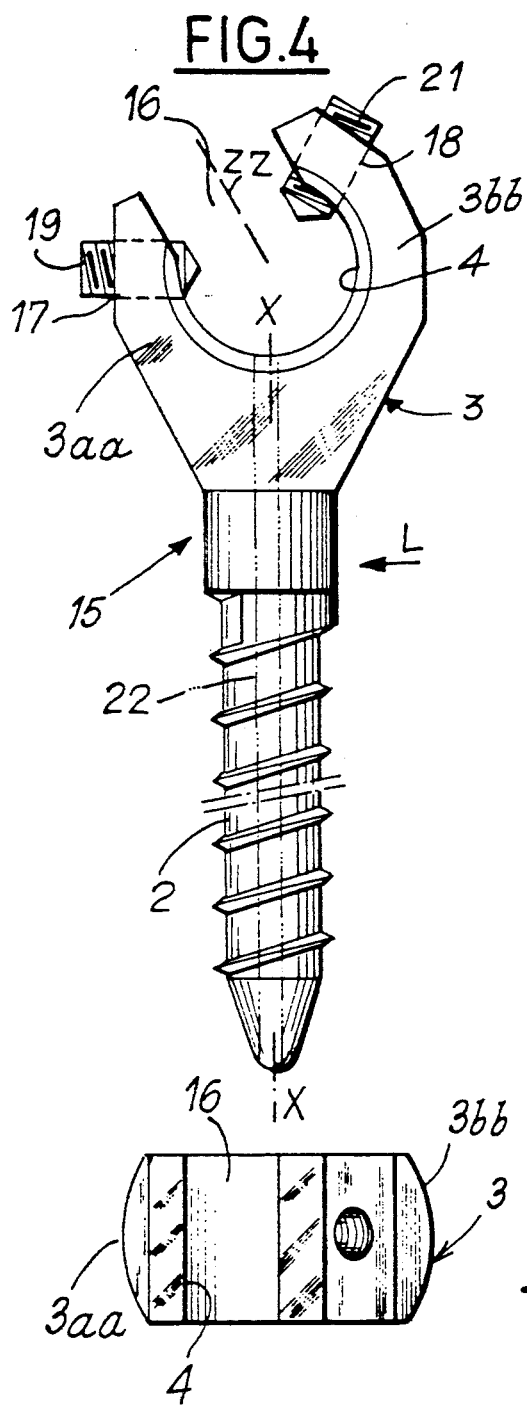

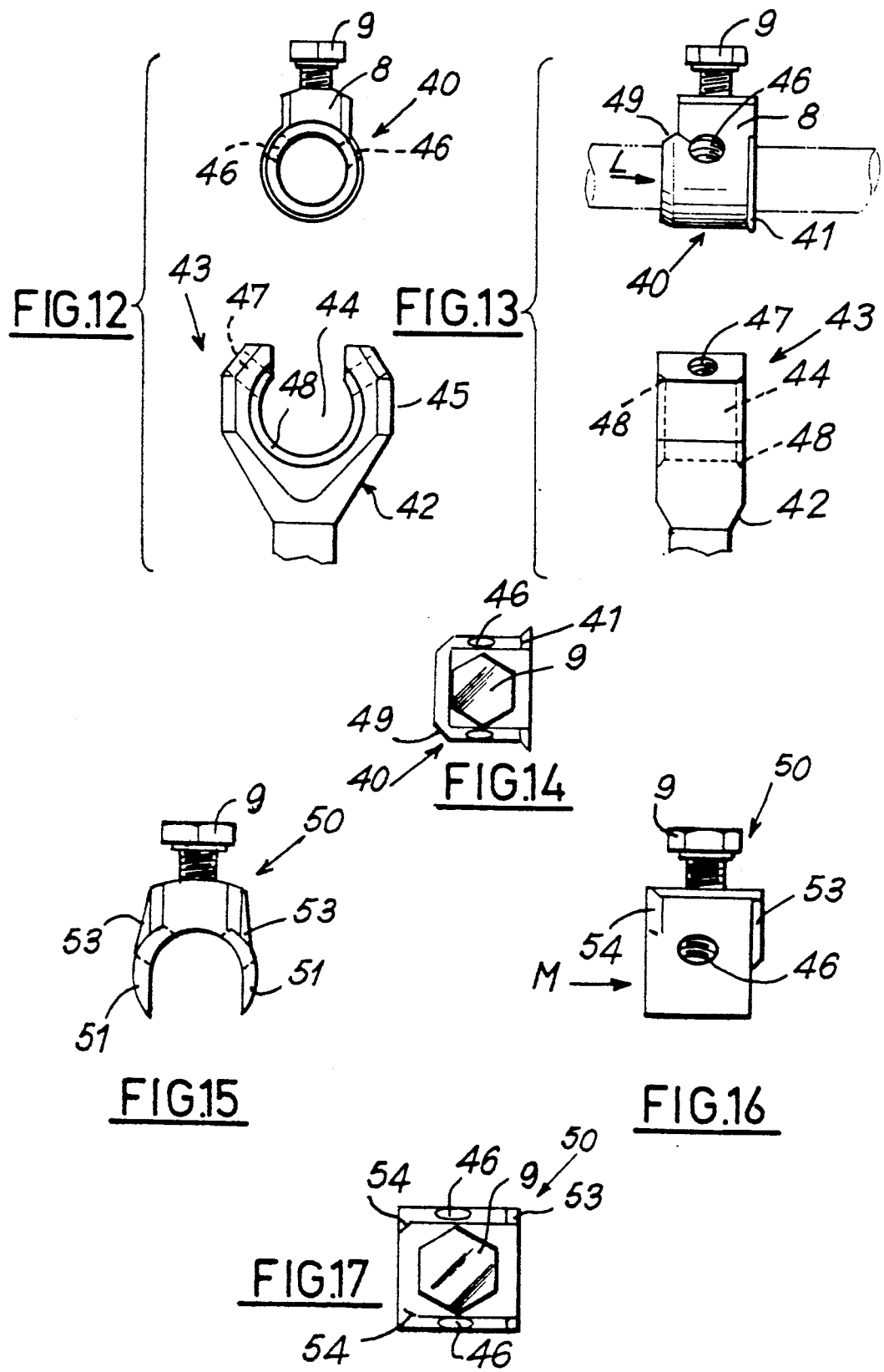

VERTEBRAL IMPLANT FOR OSTEOSYNTHESIS DEVICE

The present invention relates to a vertebral implant for an osteosynthesis device.

More precisely, this implant is of the type comprising an osseous anchoring element, consisting of a screw or of a curved plate forming a hook, a body having a channel designed to be passed through by a rod, and a first screw for securing the implant with the rod, this screw having its axis perpendicular to the rod against which it is screwed, either through the body or through a clamp able to slide on the rod and to take up a position in the body.

In spinal osteosynthesis devices it is known to use metal rods with surface roughness which permits the fixation of hooks as described in French patent 83/07,450 (U.S. Pat. No. 2,545,350), or of screws as described in French patent 87/03,485. This fixation can be effected in all positions of level, and in all directions, by means of one or two blocking screws screwed through the body of the implant on the rod. The body of the hooks and of the screws is either closed about its channel for passage of the rod or has a rear opening or a side opening leading into the channel.

The openings permit direct insertion of the rod in the channel of the body of the implant. In the case of an implant with a rear opening, the rod-implant fixation is achieved by means of an intermediate piece called a clamp, formed by a ring of which one half is conical and the other half cylindrical, with a square tapped body on top for the passage of a blocking screw and the rotational fixation (above mentioned patent 83/07,450).

The rod provided with its clamp is inserted into the channel of the implant which comes into engagement on the clamp, affording, after screwing of the latter, an implant-rod fixation. In order to prevent any displacement of the implant on its clamp on the conical end of the latter, an additional piece called a safety lock is necessary. It consists of a ring with a side opening for passage of the rod, provided with two arms partially enclosing the body of the implant and screwed directly on the rod.

This earlier device consists essentially of three relatively large pieces (hook, lock and clamp). This results in a certain difficulty in assembly, in particular at the junction of the lumbar and sacral regions where a small space is available on account of the anatomic conditions.

Moreover, in this earlier device, a risk of the clamp possibly sliding relative to the hook of the implant cannot be totally ruled out, although this is precisely the function of the safety lock.

The aim of the invention is therefore to provide an implant in which these disadvantages are overcome, and which affords a fixation of the rod in the body of the implant which is more stable than that obtained in the device of French patent 83/07,450.

According to the invention, the vertebral implant comprises at least one second screw for blocking the rod, passing through the body laterally to the first screw and engaged in a tapped hole inclined relative to the axis of the said first screw, these two screws being situated essentially in one and the same plane perpendicular to the axis of the channel and of the rod.

In one possible embodiment, two tapped holes having their axes inclined relative to the axis of the first screw are formed in the body to each side of the first screw, in order to receive corresponding blocking screws.

If the body is of the closed type, the implant does not have a clamp, and the two or three abovementioned screws pass through tapped holes formed in the body. If the body is of the type with a rear or side opening leading into the channel, the implant is equipped with a clamp which can take up a position inside the body and is provided with the first central screw, on either side of which are placed the two oblique lateral screws which are screwed directly to the rod through holes pierced in the branches of the body and in the clamp.

The rod can be fixed in the implant advantageously by three screws, namely the two oblique lateral screws and the clamp screw.

Thus, in contrast to the device of the above-mentioned earlier patent, this implant does not comprise a lock, but nevertheless guarantees a fixation on the rod in all directions and with greater stability than previously. The size of the implant thus formed is therefore significantly reduced, and this facilitates its positioning by the surgeon, in particular in the lumbar and sacral regions.

Other features and advantages of the invention will emerge in the course of the following description which is given with reference to the attached drawings which illustrate several embodiments by way of non-limiting examples.

FIG. 1 is the front view of a first embodiment of the vertebral implant according to the invention, mounted on the corresponding rod.

FIG. 2 is a front view according to arrow K in FIG. 1.

FIG. 3 is a plan view of the implant in FIGS. 1 and 2.

FIG. 4 is a front view of a second embodiment of the implant according to the invention.

FIG. 5 is a front view in the direction of arrow L in FIG. 4, and also shows in broken lines a possible variant embodiment of this implant.

FIG. 6 is a plan view of the implant in FIGS. 4 and 5.

FIG. 12 is an exploded front view of a fifth embodiment of the implant according to the invention, in the axial direction of the arrow L in FIG. 13.

FIG. 13 is a front view of the implant in FIG. 12 in a direction perpendicular to the plane of this FIG. 12.

FIG. 14 is a plan view of the clamp of the implant in FIGS. 12 and 13.

FIG. 15 is a front view of a clamp according to a sixth embodiment of the implant in the direction of the arrow M in FIG. 16.

FIG. 16 is a front view of the clamp in FIG. 15 in a plane perpendicular to that in this FIG. 15.

FIG. 17 is a plan view of the clamp in FIGS. 15 and 16.

Figure 7:
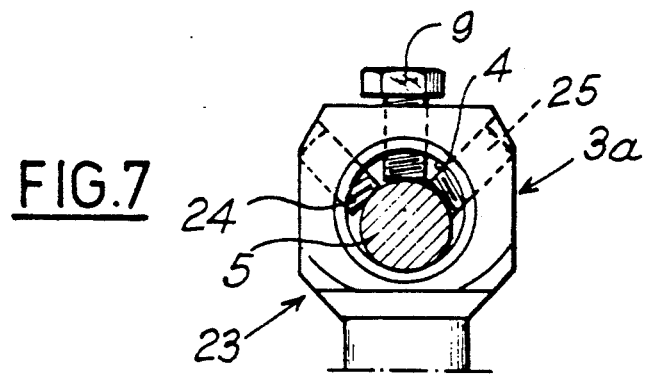
FIG. 7 is a partial front view, similar to FIG. 1, of a third embodiment of an implant according to the invention.

The vertebral implant shown in FIGS. 1 to 3 is intended for an osteosynthesis device for spinal surgery.

This implant 1 comprises an osseous anchoring element 2, here consisting of a screw of appropriate dimensions and threading. The implant 1 also comprises a body 3 integral with the screw 2, and which has a central channel 4 designed to be passed through by a rod 5 whose surface can be smooth or roughened, for example covered with diamond points. The body 3 is of the type with a rear opening 6 coaxial to the axis XX of the implant 1 and delimited by two branches 3a and 3b whose inner surfaces form edges for the channel 4.

The implant 1 is provided with an annular clamp 20 consisting of a cylindrical ring 7, of a radial extension 8 projecting from the ring 7, and of a screw 9 which can be screwed in a tapped hole in the extension 8 in order to bear on the surface of the rod 5. The inner diameter of the ring 7 is slightly greater than the diameter of the rod 5 so that the clamp 20 can slide on the latter, and this clamp is dimensioned so as to be able to engage in the channel 4 with its extension 8 placed between the ends of the branches 3a, 3b in the rear opening 6. The ring 7 is provided with a truncated front part 7a designed to fit in abutment against a complementary truncated part 11 of the channel 4.

The implant 1 is equipped with means for blocking on the rod 5 supplementary to the first central screw 9. In the example described, the means consist of a second and a third screw 12, 13 passing through the respective branches 3a, 3b of the body 3 lateral to the first screw 9 and to each side of the latter, relative to the axis to which they are inclined by a suitable angle A. The screws 12, 13 are screwed into corresponding tapped holes 12a, 13a of inclination A relative to the axis XX of the implant 1 and of the screw 9. The two blocking screws 12 and 13 are situated essentially in one and the same plane perpendicular to the axis YY of the channel 4 and of the rod 5, that is to say the plane of FIG. 1.

In a variant the implant 1 could be equipped with only one screw 12 or 13 associated with a single tapped hole, or else only one of the screws 12 and 13 can be positioned in the implant 1, in certain cases of difficult positioning in areas of the spine where space is limited. In order to permit their screwing, grooved indentations 12b, 13b, profiled in a suitable manner to receive a screwing tool, are formed in the heads of the screws 12 and 13.

The positioning of the implant 1, which has just been described, on the rod 5, is carried out in a very simple manner: the clamp 20 having been previously mounted sliding freely on the rod 5, the latter is introduced into the channel 4 via the rear opening 6. The clamp 20 is then slid until it penetrates between the branches 3a and 3b and its conical part 7a comes into abutment against the complementary part 11. The screws 9 and 12, 13 are then screwed successively, the latter two screws passing through respective holes such as 14 which are symmetrical relative to the axis XX.

The size of this implant in the direction of the rod 5 is greatly reduced compared to that of the implant described in French patent 83/07,450, in particular by virtue of the omission of the lock. Moreover, it should be noted that the walls or branches 3a, 3b of the body 3 are thickened compared to those of the body of the hook described in the abovementioned French patent, in order to increase their mechanical strength. They are also rounded in order to reduce or eliminate sharp angles capable of injuring the tissues of the patient.

The reduction in size of the implant 1 is particularly advantageous in cases where its volume can make the instrumentation difficult or impossible, for anatomic reasons, such as at the level of the sacrum. Finally, if headless screws 12, 13 are used, having indentations 12b, 13b, for example hexagonal indentations of the M3HC type (French patent 87/16,209), it is possible to remove the implanted equipment by unscrewing the two screws 12 and 13 as well as the central screw 9.

The implant 15 shown in FIGS. 4 to 6 differs from the implant 1 in that the rear opening 6 is here replaced by a side opening 16 whose axis ZZ is inclined relative to the axis XX of the implant 15 by a suitable angle, for example 25° or 30°. (These values are of course only given by way of non-limiting example and can vary very considerably). Thus, the opening 16 and the channel 4 are here delimited by lateral branches 3aa and 3bb of unequal lengths, the branch 3aa being shorter than the branch 3bb. For this reason the two tapped holes 17, 18 formed in the branches 3aa and 3bb and their corresponding screws 19, 21, inclined relative to the axis ZZ and symmetrical relative to the latter, have different inclinations relative to the axis XX. However, the positioning of the implant 15, which comprises a clamp (not shown) similar to the clamp 6, is carried out in the same manner as for the implant 1.

As in the above embodiment, the implant 15 can comprise only a single tapped hole 17 or 18, or comprise two of them but only be used with one of the screws 19 and 21.

According to a possible variant design, the base of the channel 4 can be connected to the end of the screw 2 by way of an axial conduit 22 for guiding the implantation of the screw and the body by means of a rod (not shown) engaged in this conduit 22.

According to another possible variant (FIG. 5), the screw 2 is replaced by a screw 2a inclined at a suitable angle to the axis XX and thus forming an obtuse angle to the body 3. The implant thus formed is designed to be used in the sacrum for oblique fixation.

The third embodiment of the implant 23 shown in FIG. 7 comprises a closed body 3a and is consequently without a clamp. The central screw 9 is introduced here through the body 3a in a central position as in the above embodiments and is screwed onto the rod 5, on which there also bear two oblique screws 24, 25 symmetrical relative to the screw 9 and passing through corresponding tapped holes in the body 3a.

All these embodiments of the implant according to the invention have in common the saving in space and greater ease of assembly, as well as better stability of fixation than the known implants described in the above-mentioned patents.

Figure 8:
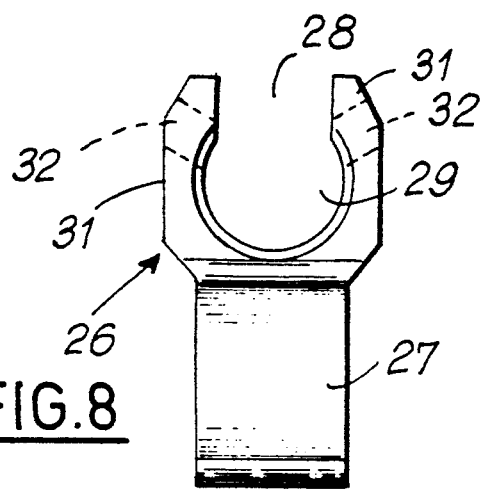
FIG. 8 is a front view of a fourth embodiment of the implant according to the invention, in which the osseous anchoring element is a hook.
Figure 9:
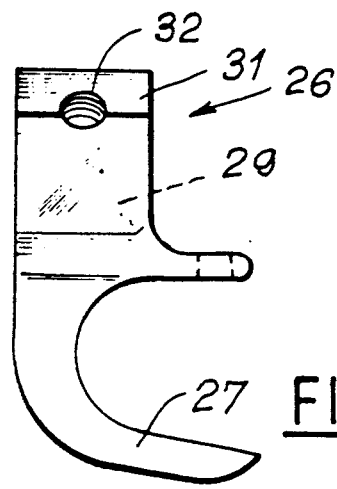
FIG. 9 is a side view of the implant in FIG. 8.

The implant 26 in FIGS. 8 and 9 is a hook made up of a curved plate 27 and of a body with a rear opening 28 and channel 29 delimited by two branches 31 pierced with two oblique tapped holes 32 for receiving screws which are not shown (nor is the clamp, which is similar to the clamp 20).

Figure 10:
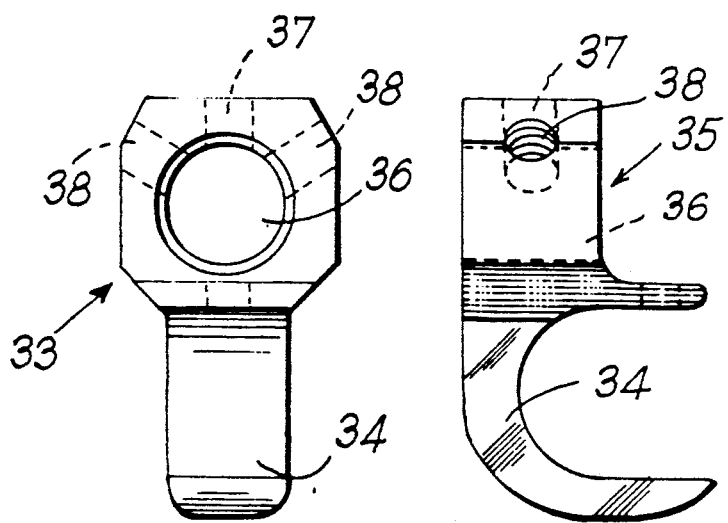
FIGS. 10 and 11 are views, similar to FIGS. 8 and 9, of a hook implant variant.
Figure 11:
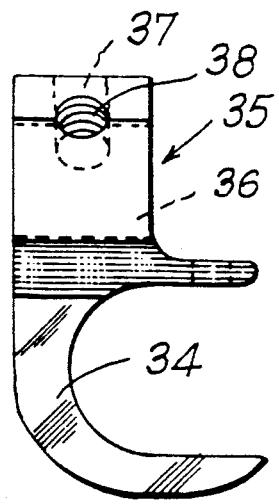

The implant in FIGS. 10 and 11 is also a hook 33 with a plate 34, but its body 35 is closed. It is pierced with a channel 36 and three tapped holes 37, 38 for passage of the screws.

In another variant, the truncated parts 7a and 11 can be replaced by any appropriate male and female parts.

In the embodiment in FIGS. 12 to 14, the clamp 40 is annular and is provided at one of its ends with a radially projecting abutment 41. This abutment 41 can take the form of a collar designed to bear on the body 42 of the implant 43 and, more precisely, on one of the ends of its channel 44, the body 42 being of the open type with its channel 44 delimited by two lateral branches 45. The function of the abutment 41, by bearing against the inlet edge of the channel 44, is to position the clamp 40 correctly in the body 42 so that the tapped holes 46 for passage of the lateral screws in the clamp 40 come into exact alignment with the holes 47 in the body 42.

Bevels 48 can advantageously be formed on the opposite edges of the openings of the channel 44 in order to facilitate the introduction of the clamp 40 into the body 42. In this case the end of the clamp 40 opposite its end bearing the abutment 41 has a complementary bevel 49, while the abutment 41 is profiled as a conical chamfer or bevel in order to be able to bear on one of the bevels 48 at the inlet of the channel 44.

If no bevel 48 is formed on the body 42, the abutment 41 can be, for example, circular or have a square cross-section.

Since the channel 44 is cylindrical along its entire length and is enlarged at each of its ends by means of a bevel 48, it is possible to introduce the clamp 40 into the body 42 by way of one or other of the openings of the channel 44.

The clamp 50 shown in FIGS. 15 to 17 is made in the form of a rider with two legs 51 which delimit between them a channel 52 open radially in the direction opposite the central screw 9. The lateral legs 51 and the semicircular profile of the channel 52 are designed to cover the rod (not shown) by enclosing it between the legs 51. The clamp 50 is additionally provided with a radially projecting abutment taking the form, in this example, of two lateral excrescences 53 designed to bear on the body of the implant in order to position the clamp 50 in a satisfactory manner relative to the latter. It will be noted that the excrescences 53 are formed in such a way that their surfaces form a tangent to the ends of the legs 51. Moreover, a bevel 54 is formed on each side of the end of the clamp 50 opposite its end bearing the abutment excrescences 53. The bevelled parts 54 facilitate the introduction of the clamp 50 into the body of the implant.

By virtue of the design of the clamp 50 as a rider with a radially open channel 52, it is possible to position this clamp on the corresponding rod after introduction of the latter into the body of the implant, covering it by means of this clamp 50. In fact, when the clamp consists of a closed cylinder, it is obviously necessary to engage it on the rod prior to the introduction of the latter into the body of the implant.

I claim:

1. A vertebral implant for an osteosynthesis device, comprising:
   an osseous anchoring element; and
   a rod securing portion connected to said osseous anchoring element for securing a rod relative to said osseous anchoring element, said rod securing portion including a body member having a channel extending therethrough for receiving a rod therein, a first screw means including a first screw for securing the rod in said channel, said first screw extending radially relative to said channel, and at least one second screw for further securing the rod in said channel, said body member having a tapped hole inclined relative to said first screw threadedly receiving said second screw therein, and both said first screw and said at least one second screw being substantially disposed in a plane perpendicular to the axis of said channel.

2. The vertebral implant of claim 1, and further comprising a second tapped hole in said body on a side of said first screw opposite to that of the first said tapped hole, said second tapped hole being inclined relative to said first screw for receiving a further said second screw therein.

3. The vertebral implant of claim 1, wherein:
   said body member comprises an open portion defined by two branch portions, said branches further defining said channel except at said open portion;
   said tapped hole extends through one of said branch portions; and
   said first screw means is an annular clamp attachable to and from said body member in said open portion defined by said two branch portions, said annular clamp having a tapped hole for receiving said first screw therethrough and a further hole alignable with said tapped hole of said body member for receiving a said second screw therethrough.

4. The implant of claim 3, wherein said clamp has an abutting member and said channel of said body has an abutment so that said abutting member abuts against said abutment when said clamp is attached to said body member, and said clamp further has a radial extension for disposition in said open portion of said body member.

5. The implant of claim 1, wherein:
   said osseous anchoring element is a screw extending perpendicular to said channel;
   said screw has an axial conduit extending therethrough for said channel to the distal end of said screw for guiding the implantation thereof; and
   said body member comprises an open portion defined by two branch portions thereof, said tapped hole extending through one of said branch portions.

6. The implant of claim 1, wherein said body member lies in a plane, and said osseous anchoring element is a screw extending at an obtuse angle relative to said plane of said body member.

7. The implant of claim 1, wherein said osseous anchoring element is a curved plate.

8. The implant of claim 1, wherein said first screw means comprises an annular clamp attachable to and from said body member and having a radially projecting abutment for contacting said body member for positioning said annular clamp relative to said body member.

9. The implant of claim 8, wherein said abutment is a collar.

10. The implant of claim 8, wherein said channel has opposite openings thereof, each said channel opening having a bevelled edge for facilitating introduction of said clamp into said channel of said body member, said annular clamp has a complimentarily bevelled end thereof opposite to said radially projecting abutment and said radially projecting abutment has a profile corresponding to and for bearing on one of said bevelled edges.

11. The implant of claim 1, wherein said first screw means comprises a clamp attachable to and from said body member having a central portion and two legs extending from said central portion for covering and enclosing a rod in a radially open channel defined by said central portion and said legs after positioning of the rod in said channel of said body member.

12. The implant of claim 11, wherein said clamp has a radially projecting abutment for contacting said body member for positioning said annular clamp relative to said body member.

13. The vertebral implant of claim 1, wherein:

said body member comprises an open portion defined by two branch portions, said branches further defining said channel except at said open portion;

said tapped hole extends through one of said branch portions; and said first screw means is a clamp attachable to and detachable from said body member in said open portion defined by said two branch portions and in said channel, said clamp having a tapped hole for receiving said first screw therethrough and a further hole alignable with said tapped hole of said body member for receiving a said second screw therethrough.

14. The vertebral implant of claim 13, wherein said clamp has a central portion and two legs extending from said central portion for covering and enclosing a rod in a radially open channel defined by said central portion and said legs after positioning of the rod in said channel of said body member.

15. The vertebral implant of claim 1, wherein said first screw means comprises a tapped hole in an upper central portion of said body member receiving said first screw therein, said upper central portion formed as one piece and integral with said body member.

* * * * *